(12) United States Patent
Yamada et al.

(10) Patent No.: US 8,790,306 B2
(45) Date of Patent: Jul. 29, 2014

(54) INJECTION EQUIPMENT AND MEDICAL LIQUID INJECTING SYSTEM HAVING SAME

(75) Inventors: Keiichi Yamada, Izumi (JP); Masayuki Uruma, Izumi (JP); Masaki Hiramatsu, Izumi (JP)

(73) Assignee: Daiken Iki Kanbushiki Kaisha (JP)

( * ) Notice: Subject to any disclaimer, the term of this patent is extended or adjusted under 35 U.S.C. 154(b) by 0 days.

(21) Appl. No.: 13/515,395

(22) PCT Filed: Dec. 15, 2010

(86) PCT No.: PCT/JP2010/007275
§ 371 (c)(1),
(2), (4) Date: Jun. 12, 2012

(87) PCT Pub. No.: WO2011/074255
PCT Pub. Date: Jun. 23, 2011

(65) Prior Publication Data
US 2012/0253283 A1  Oct. 4, 2012

(30) Foreign Application Priority Data

Dec. 16, 2009 (JP) ................................ 2009-285292

(51) Int. Cl.
| | | |
|---|---|---|
| *A61M 37/00* | (2006.01) | |
| *A61M 5/142* | (2006.01) | |
| *A61M 5/168* | (2006.01) | |
| *A61M 5/145* | (2006.01) | |

(52) U.S. Cl.
CPC ......... *A61M 5/1424* (2013.01); *A61M 5/16809* (2013.01); *A61M 2005/14506* (2013.01)
USPC ........................................................ 604/133

(58) Field of Classification Search
USPC ........... 604/131, 132, 133, 246, 248, 249, 30, 604/32, 33, 48, 8–10
See application file for complete search history.

(56) References Cited

U.S. PATENT DOCUMENTS

| | | | |
|---|---|---|---|
| 5,011,477 | A | 4/1991 | Winchell et al. |
| 5,360,411 | A | 11/1994 | Mimura et al. |
| 5,807,337 | A | 9/1998 | Yamada et al. |
| 7,611,496 | B2 | 11/2009 | Yamada et al. |
| 2006/0150725 | A1 | 7/2006 | Yamada et al. |

FOREIGN PATENT DOCUMENTS

| | | |
|---|---|---|
| JP | 3-505538 | 12/1991 |
| JP | 6-121835 | 5/1994 |
| JP | 2002-58739 | 2/2002 |
| JP | 2003-111839 | 4/2003 |
| JP | 2004-147862 | 5/2004 |
| WO | 95/28977 | 11/1995 |

OTHER PUBLICATIONS

JP 2002058739, Namiki et al., date of publication: Feb. 26, 2002.*

* cited by examiner

*Primary Examiner* — Manuel Mendez
(74) *Attorney, Agent, or Firm* — Gerald E. Hespos; Michael J. Porco; Matthew T. Hespos

(57) ABSTRACT

Provided is a injection equipment capable of alleviating the force required of a user to inject a medical liquid. A housing chamber S1 for extrusion and a housing chamber S2 for injection are mutually connected so that, when one of the chambers S1, S2 expands, the other one of the chambers contracts. As a result of switching a switching valve 9 to an open position in a state where at least a predetermined amount of the medical liquid is filled in the housing chamber S2, the housing chamber S2 for injection is contracted based on the expansion of the housing chamber S1 for extrusion according to the discharge pressure of the medical liquid pump 2 so as to deliver a predetermined amount of medical liquid.

8 Claims, 9 Drawing Sheets

INJECTION EQUIPMENT AND MEDICAL LIQUID INJECTING SYSTEM HAVING SAME

TECHNICAL FIELD

The present invention relates to an injection equipment for filling a predetermined amount of a medical liquid discharged from a medical liquid injection device, and delivering the predetermined amount of medical liquid according to a user's operation.

BACKGROUND ART

As a conventional injection equipment, for example, Japanese Unexamined Patent Publication No. H03-505538 discloses an assembly including liquid source supplying means for supplying a pressured liquid source, a bolus dose device for providing a liquid of a controlled bolus dose, and means for adjusting the steady flow rate of the liquid. The bolus dose device includes a dose reservoir capable of filling the liquid supplied from the liquid source supply means. This dose reservoir can discharge its contents by being compressed.

Nevertheless, with the bolus dose device of Japanese Unexamined Patent Publication No. H03-505538, there is a problem in that considerable force is required of the user to inject the medical liquid filled in the dose reservoir into the patient's body. Specifically, in order to inject the medical liquid filled in the dose reservoir into the patient, the medical liquid needs to be forced through members such as a filter or a catheter having large circulation resistance. In addition, the force required for compressing the dose reservoir in order to generate this flow is extremely large.

SUMMARY OF THE INVENTION

The present invention was devised in view of the foregoing problems, and an object of this invention is to provide an injection equipment and a medical liquid injection system comprising such an injection equipment capable of alleviating the force required for a user to inject a medical liquid.

In order to achieve the foregoing object, the present invention provides an injection equipment which is to be connected to a discharge unit capable of discharging a pressured medical liquid, and which fills the medical liquid from the discharge unit and delivers a predetermined amount of the medical liquid according to operation of a user, the injection equipment having: an introductory passage which is connectable to the discharge unit and which is used for guiding the medical liquid from the discharge unit; a housing chamber for extrusion which is capable of housing the medical liquid guided by the introductory passage and which is expandable according to the housing of the medical liquid; a housing chamber for injection which can be communicated with the discharge unit via an adjustable unit for adjusting a flow rate of the medical liquid discharged from the discharge unit and which expands according to the housing of the medical liquid, and which can deliver the housed medical liquid by being contracted; a delivery passage for guiding the medical liquid delivered from the housing chamber for injection to a patient; a switching valve capable of performing a switching operation between a closed position for preventing the delivery of the medical liquid through the delivery passage, and an open position for allowing the delivery of the medical liquid through the delivery passage; and an operating part capable of switching the switching valve from the closed position to the open position by receiving operation of user in a state where the predetermined amount of medical liquid is housed in the housing chamber for injection, wherein the housing chamber for extrusion and the housing chamber for injection are mutually connected so that, when one of the chambers expands, the other one of the chambers contracts, and wherein, by switching the switching valve to the open position in a state where at least the predetermined amount of medical liquid is filled in the housing chamber for injection, the housing chamber for injection is contracted based on the expansion of the housing chamber for extrusion according to the discharge pressure from the discharge unit so as to deliver the predetermined amount of medical liquid.

Moreover, the present invention provides a medical liquid injection system comprising a discharge unit capable of discharging a pressured medical liquid, and the injection equipment connected to the discharge unit.

BEST MODE FOR CARRYING OUT THE INVENTION

Embodiments of the present invention are now explained with reference to the appended drawings. Note that the following embodiments are merely examples of embodying the present invention, and are not intended to limit the technical scope of the present invention.

The preferred embodiments of the present invention are now explained with reference to the drawings.

Figure 1:
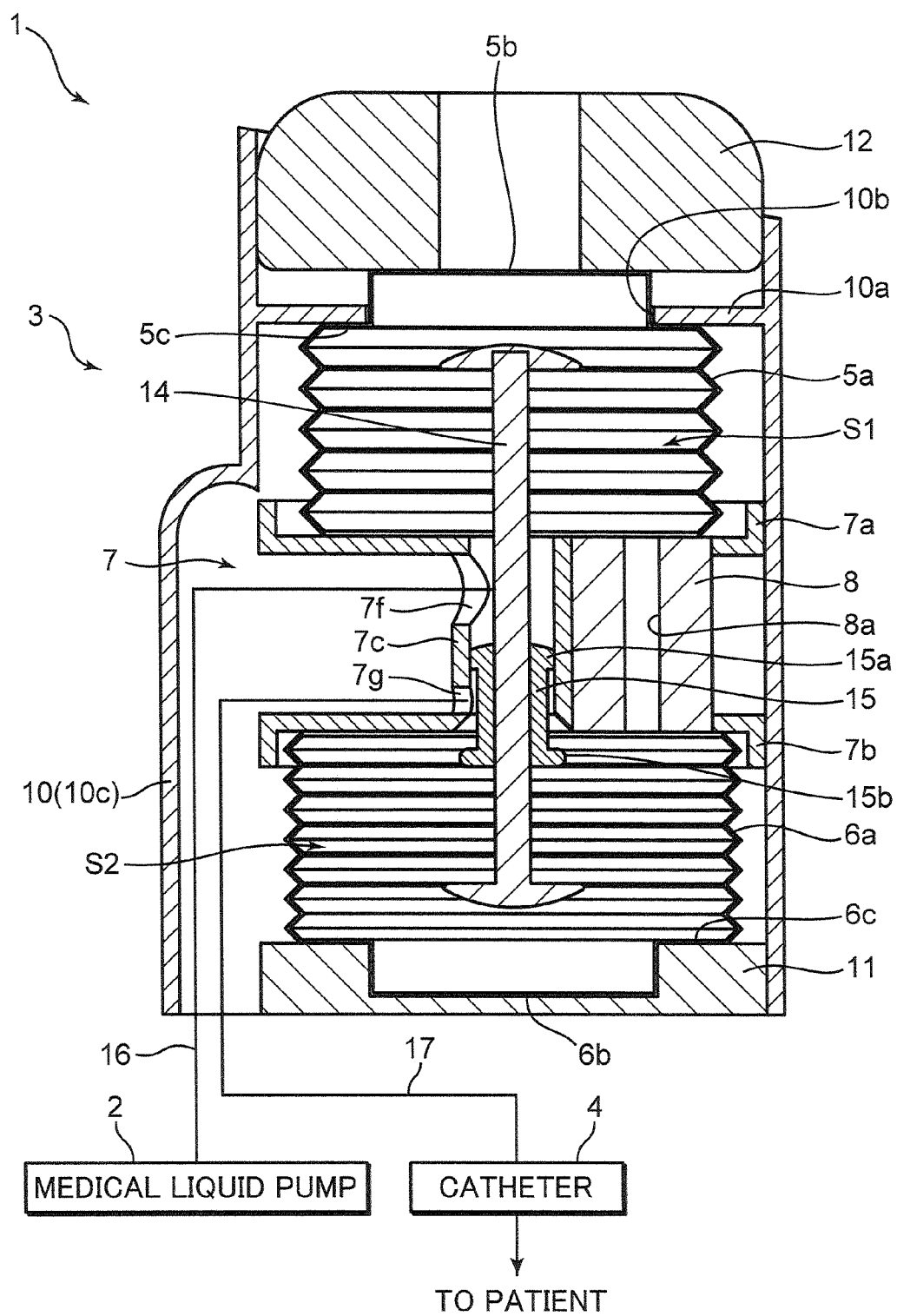
FIG. 1 is a schematic diagram showing the overall configuration of the medical liquid injection system according a preferred embodiment of the present invention.
Figure 2:
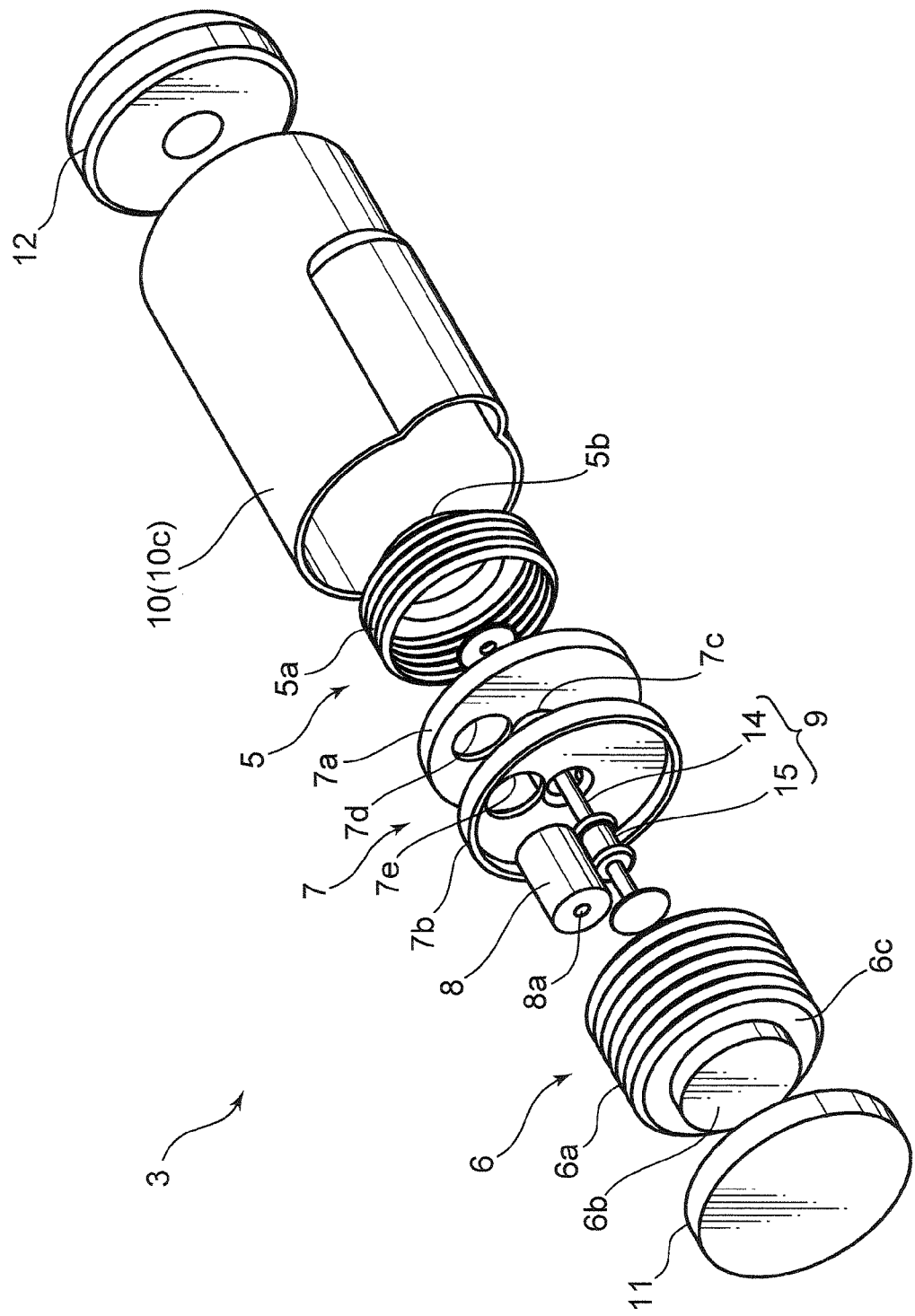
FIG. 2 is an exploded perspective view of the injection equipment depicted in FIG. 1.

FIG. 1 is a schematic diagram showing the overall configuration of the medical liquid injection system according a preferred embodiment of the present invention. FIG. 2 is an exploded perspective view of the injection equipment depicted in FIG. 1.

Referring to FIG. 1 and FIG. 2, a medical liquid injection system 1 comprises a medical liquid pump (discharge unit) 2 capable of discharging a pressured medical liquid, an injection equipment 3 connected to the medical liquid pump 2, and which fills the medical liquid from the medical liquid pump 2 and delivers a predetermined amount of the medical liquid according to a user's operation, and a catheter 4 for guiding the medical liquid delivered from the injection equipment 3 to a patient.

The medical liquid pump 2 includes a housing part for housing the medical liquid, and discharges the medical liquid in the housing part in a state where the medical liquid is pressurized to a predetermined pressure. Specifically, as the medical liquid pump 2, for instance, used may be the type disclosed in WO 95/28977 which uses atmospheric pressure as the drive source, the type disclosed in Japanese Patent Application Publication No. 2004-147862 which uses the resilience of a flexible container as the drive force, or a type which uses the bias force of an elastic member such as a spring as the drive force.

The injection equipment 3 comprises an introductory tube (introductory passage) 16 connected to the medical liquid pump 2, an accordion container 5 for extrusion capable of housing the medical liquid that was guided by the introductory tube 16, an accordion container 6 for injection for filling a predetermined amount of the medical liquid to be injected into a patient, a connecting member 7 for connecting both accordion containers 5, 6, an adjustable member (adjustable unit) 8 and a switching valve 9 provided to the connecting member 7, a delivery tube (delivery passage) 17 for causing the accordion container 6 for injection and the catheter 4 to be in communication, a cylindrical container (fixing member) 10 and a lid body (fixing member) 11 for fixing the positions of outer end faces of both accordion containers 5, 6 which are mutually separated, and an operation button (operating part) 12 provided to one end of the cylindrical container 10 so as to enable a pushing operation.

The accordion container 5 for extrusion can expand and contract along a telescopic shaft of a predetermined direction (up-and-down direction of FIG. 1). Moreover, with the accordion container 5 for extrusion, one side of its expansion/contraction direction (upper side of FIG. 1) is closed, and the other side of its expansion/contraction direction (lower side of FIG. 1) is open. Specifically, the accordion container 5 for extrusion comprises a cylindrical accordion body 5a capable of expanding and contracting along the telescopic shaft, a bottom part 5c which closes one side of the expansion/contraction direction of the accordion body 5a, and a protruding part 5b provided to the bottom part 5c. The protruding part 5b has a diameter size that is smaller than the bottom part 5c and protrudes to one side (upward in FIG. 1) of the expansion/contraction direction. A housing chamber S1 for extrusion is provided inside the accordion container 5 for extrusion.

The accordion container 6 for injection is capable of expanding and contracting along a telescopic shaft of a predetermined direction (up-and-down direction of FIG. 1). Moreover, with the accordion container 6 for injection, one side of its expansion/contraction direction (lower side of FIG. 1) is closed, and the other side of its expansion/contraction direction (upper side of FIG. 1) is open. Specifically, the accordion container 6 for injection comprises a cylindrical accordion body 6a capable of expanding and contracting along the telescopic shaft, a bottom part 6c which closes one side of the expansion/contraction direction of the accordion body 6a, and a protruding part 6b provided to the bottom part 6c. The protruding part 6b has a diameter size that is smaller than the bottom part 6c and protrudes to one side (downward in FIG. 1) of the expansion/contraction direction. Note that the diameter size E2 (refer to FIG. 3) of the accordion body 6a of the accordion container 6 for injection is larger than the diameter size E1 of the accordion body 5a of the accordion container 5 for extrusion. A housing chamber S2 for injection is provided inside the accordion container 6 for injection.

The connecting member 7 connects both accordion containers 5, 6 so that, by one of both accordion containers 5, 6 expanding, the other contracts. Specifically, the connecting member 7 comprises a pair of disk part 7a and disk part 7b having substantially the same diameter size, and a connecting part 7c which concentrically connects the disk parts 7a, 7b. An end face of the opening side of the accordion body 5a of the accordion container 5 for extrusion is bonded to the surface (upper surface of FIG. 1) of the disk part 7a in a state of being matched with each other. Moreover, the disk part 7a includes a through-hole 7d which penetrates the top and bottom (upper and lower in FIG. 1) at the position to become the inner side of the accordion body 5a. An end face of the opening side of the accordion body 6a of the accordion container 6 for injection is bonded to the surface (lower surface of FIG. 1) of the disk part 7b in a state of being matched with each other. Moreover, the disk part 7b includes a through-hole 7e which penetrates the top and bottom (upper and lower in FIG. 1) at the position to become the inner side of the accordion body 6a. The connecting part 7c connects the mutually opposing faces of the respective disk parts 7a, 7b (lower face of the disk part 7a and upper face of the disk part 7b in FIG. 1) at substantially the center position of the respective disk parts 7a, 7b. Since the respective disk parts 7a, 7b and the connecting part 7c have a hole formed at the center position of the respective parts 7a to 7c, both accordion containers 5, 6 are in mutual communication through such hole. Moreover, as shown in FIG. 1, the connecting part 7c is provided with an introductory opening 7f that penetrates its side wall, and a delivery opening 7g that penetrates the side wall more close to the accordion container 6 for injection than the introductory hole 7f. The introductory tube 16 is connected to the introductory hole 7f, and the delivery tube 17 is connected to the delivery opening 7g.

The adjustable member 8 is a cylindrical member including a pore 8a, and configures the passage that causes both accordion containers 5, 6 to be in communication. Specifically, one end (upper end of FIG. 1) of the adjustable member 8 is bonded to the disk part 7a in a state of being inserted into the through-hole 7d of the disk part 7a so as to prevent the circulation of the medical liquid between the through-hole 7d and the outer face of the adjustable member 8. Moreover, the other end (lower end of FIG. 1) of the adjustable member 8 is bonded to the disk part 7b in a state of being inserted into the through-hole 7e of the disk part 7b so as to prevent the circulation of the medical liquid between the through-hole 7e and the outer face of the adjustable member 8.

The switching valve 9 is disposed across both accordion containers 5, 6 through the connecting part 7c of the connecting member 7. Specifically, the switching valve 9 comprises a valve body 15 for switching between the opening and closing of the delivery opening 7g, and an operated part 14 which extends from the valve body 15 toward both accordion containers 5, 6, and the valve body 15 is displaced as a result of the operated part 14 being pushed by the operation button 12 described later. The valve body 15 is an elastic member including a pair of flange parts 15a, 15b protruding in the circumferential direction. The flange parts 15a, 15b are respectively attached firmly to the wall surface of the connecting part 7c. It is thereby possible to restrict the flow of the medical liquid between the respective flange parts 15a, 15b and the wall surface of the connecting part 7c, and allow the flow of the medical liquid between the flange parts 15a, 15b. In addition, the valve body 15 can be displaced between the closed position shown in FIG. 3 and the open position shown in FIG. 1. In the closed position shown in FIG. 3, the flow of the medical liquid from the accordion container 6 for injection to the delivery tube 17 is prevented as a result of the respective flange parts 15a, 15b contacting tightly to the inner wall surface of the connecting part 7c at positions on both sides where the delivery opening 7g is sandwiched therebetween. Meanwhile, in the open position shown in FIG. 1, the flow of the medical liquid from the accordion container 6 for injection toward the delivery tube 17 is allowed as a result of the flange part 15b being disposed in the accordion container 6 for injection and only the flange part 15a contacting tightly to the inner wall surface of the connecting part 7c. Note that, in both the closed position and the open position, since the flange part 15a is contacted tightly to the inner wall surface of the connecting part 7c between the introductory opening 7f and the delivery opening 7g, the circulation of the medical liquid between the accordion container 5 for extrusion and the accordion container 6 for injection is restricted. The operated part 14 is fixed to the valve body 15. Although this will be explained in detail later, the length of the operated part 14 is set as follows. The protruding length of the operated part 14 from the valve body 15 toward the accordion container 5 for extrusion is the length that it will be disposed in the protruding part 5b (higher than the positioning part 10a of the cylindrical container 10 described later) of the accordion container 5 for extrusion in a state where a predetermined amount of the medical liquid is housed in the accordion container 6 for injection. The protruding length of the operated part 14 from the valve body 15 toward the accordion container 6 for injection is the length that the valve body 15 is pressed to the closed position as a result of coming into contact with the bottom face (lower face of FIG. 1) of the accordion container 6 for injection in a state where a predetermined amount of the medical liquid is delivered from the accordion container 6 for injection.

As a result of the lid body 11 being mounted on the cylindrical container 10, the cylindrical container 10 houses both accordion containers 5, 6, the connecting member 7, the adjustable member 8 and the switching valve 9 while fixing the positions of the end faces (bottom parts 5c, 6c) on the side that both accordion containers 5, 6 which are mutually separated between the cylindrical container 10 and the lid body 11.

Specifically, as shown in FIG. 1, the cylindrical container 10 comprises a cylindrical body 10c, a positioning part 10a protruding inward near one end of the body 10c (position that is slightly lower than the upper end), and a circular through-hole 10b for penetrating the top and bottom (up and down of FIG. 1) of the positioning part 10a. The body 10c is of a thickness that enables the housing of both accordion containers 5, 6 and the connecting member 7. More specifically, the inner diameter size of the body 10c is set to a size where the connecting member 7, which is larger than both accordion containers 5, 6, can slide therein. The through-hole 10b is of a size that enables the insertion of the protruding part 5b of the accordion container 5 for extrusion. In other words, the positioning part 10a fixes the position of the bottom part 5c so as to prevent the bottom part 5c of the accordion container 5 for extrusion from moving in the expanding direction (upward in FIG. 1) in a state where the protruding part 5b is inserted therethrough. Note that the protruding part 5b that is inserted through the through-hole 10b is disposed higher than the positioning part 10a and can be pressed by the operation button 12 described later.

Meanwhile, the lid body 11 is mounted on the end (lower end of FIG. 1) of the cylindrical container 10 so as to cover the opening of the cylindrical container 10. The lid body 11 includes a concave part for housing the protruding part 6b of the accordion container 6 for injection. In addition, the lid body 11 supports the bottom part 6c of the accordion container 6 for injection in a state of housing the protruding part 6b in its concave part. Specifically, the lid body 11 fixes the position of the bottom part 6c so as to prevent the bottom part 6c of the accordion container 6 for injection from moving in the expanding direction (downward in FIG. 1).

The operation button 12 is inserted into the body 10c of the cylindrical container 10 from the opening on the side (upper side of FIG. 1) to which the lid body 11 is not mounted. Moreover, the operation button 12 can slide relative to the body 10c along the expansion/contraction direction of both accordion containers 5, 6. Specifically, the operation button 12 can slide relative to the body 10c between the non-operated state shown in FIG. 1 and the operated state shown in FIG. 6. In the non-operated state shown in FIG. 1, a part of the operation button 12 is pushed upward from the body 10c by the protruding part 5b of the accordion container 5 for extrusion protruding from the positioning part 10a. Meanwhile, in the operated state shown in FIG. 6, the operation button 12 is subject to external force and is pushed into the body 10c until it comes into contact with the positioning part 10a while pressing the protruding part 5b.

Figure 3:
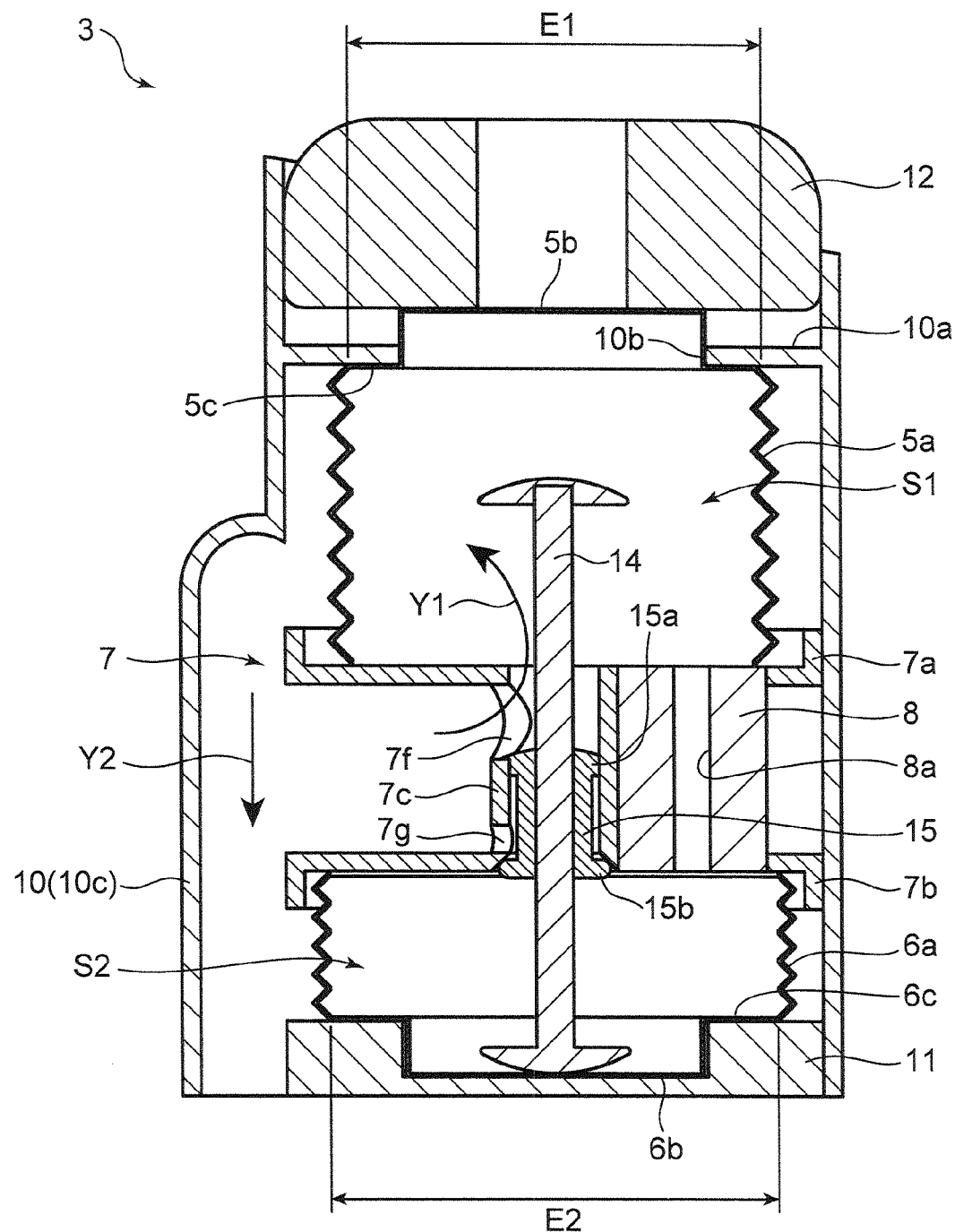
FIG. 3 is a cross section showing the operation of the injection equipment depicted in FIG. 1, and shows the state after the discharge is complete (upon initial filling).
Figure 4:
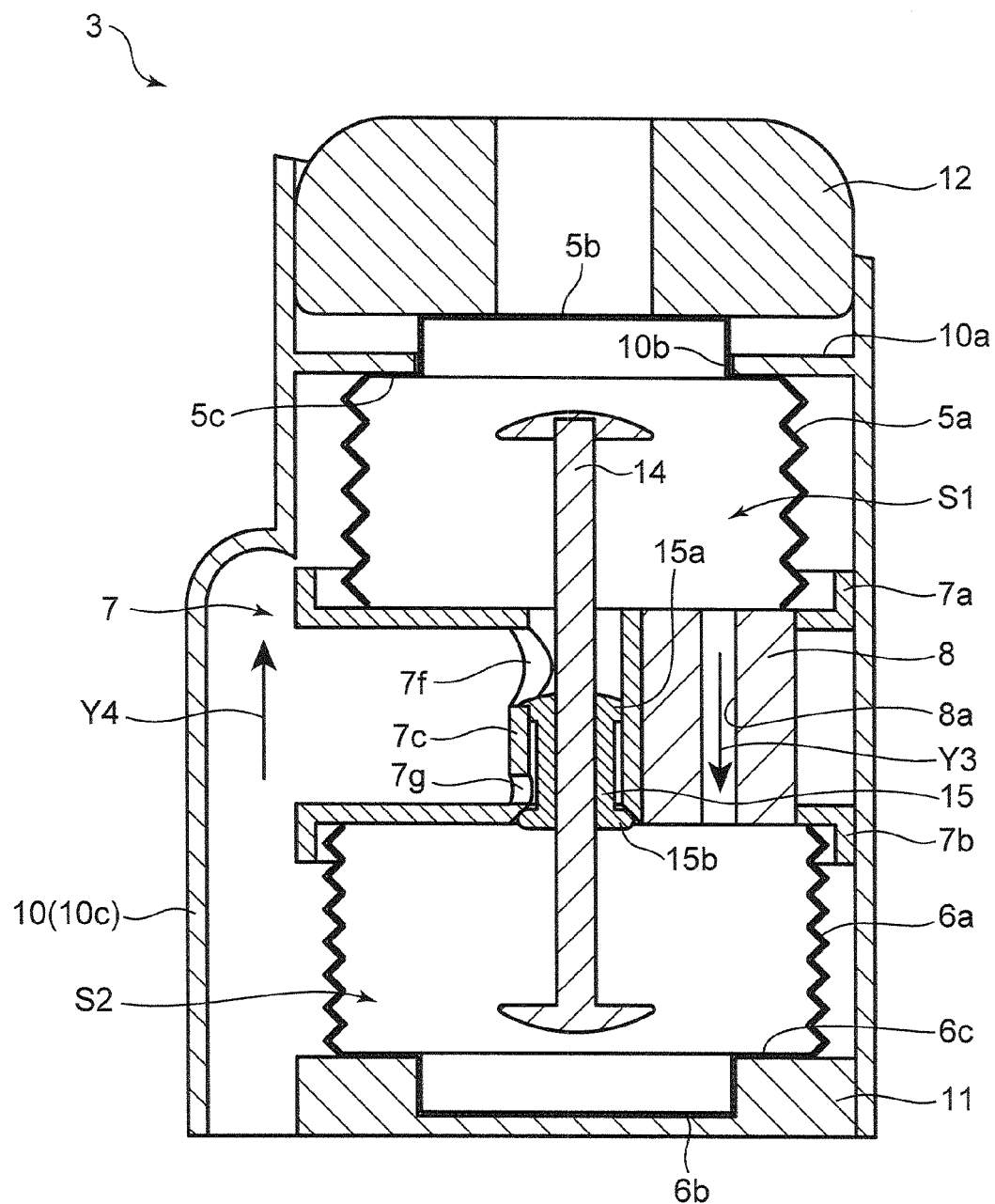
FIG. 4 is a cross section showing the operation of the injection equipment depicted in FIG. 1, and shows the state during the period of filling the medical liquid into the accordion container for injection.
Figure 5:
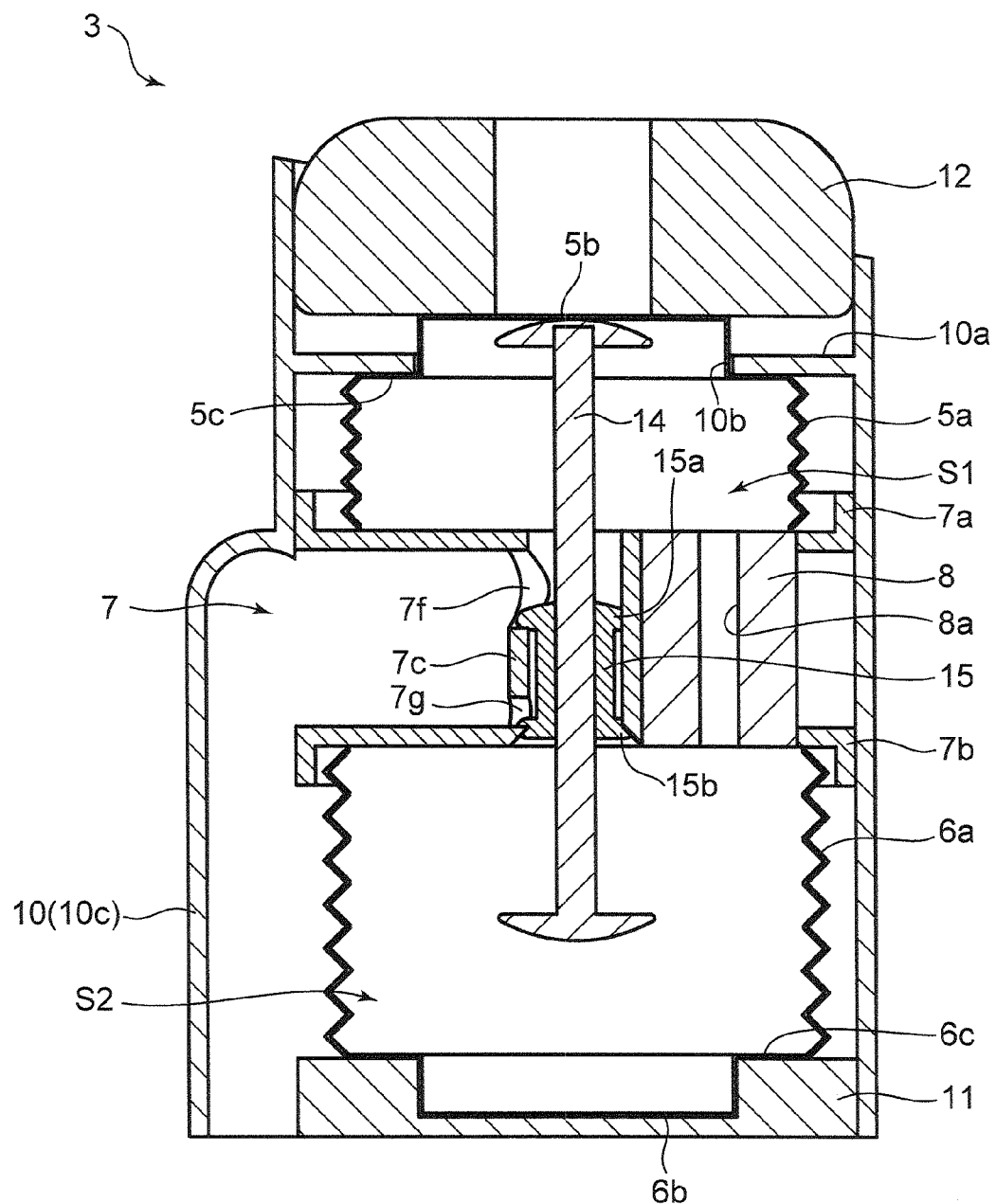
FIG. 5 is a cross section showing the operation of the injection equipment depicted in FIG. 1, and shows the state upon completion of filling the medical liquid into the accordion container for injection.
Figure 6:
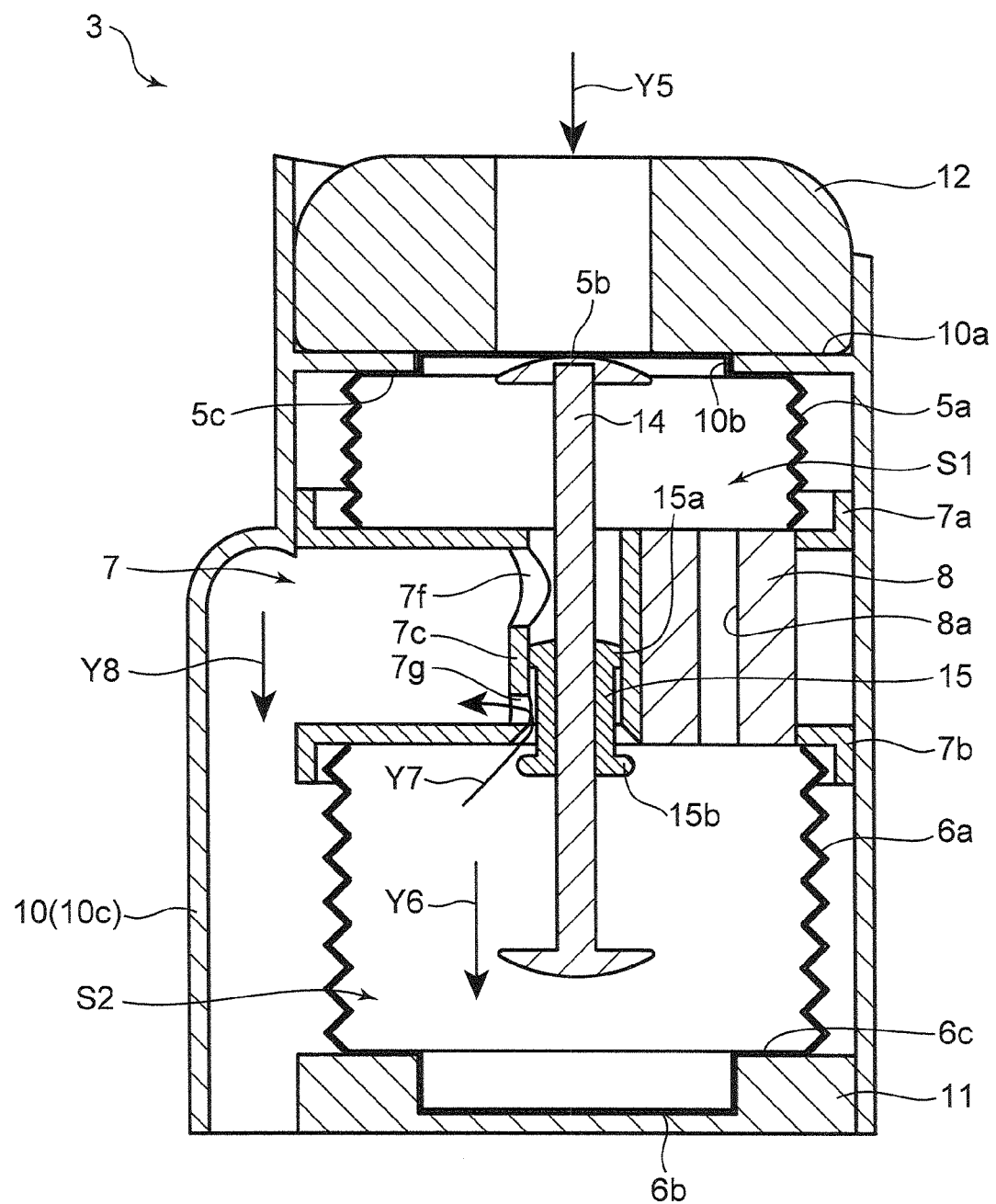
FIG. 6 is a cross section showing the operation of the injection equipment depicted in FIG. 1, and shows the state when the operation button is operated.
Figure 7:
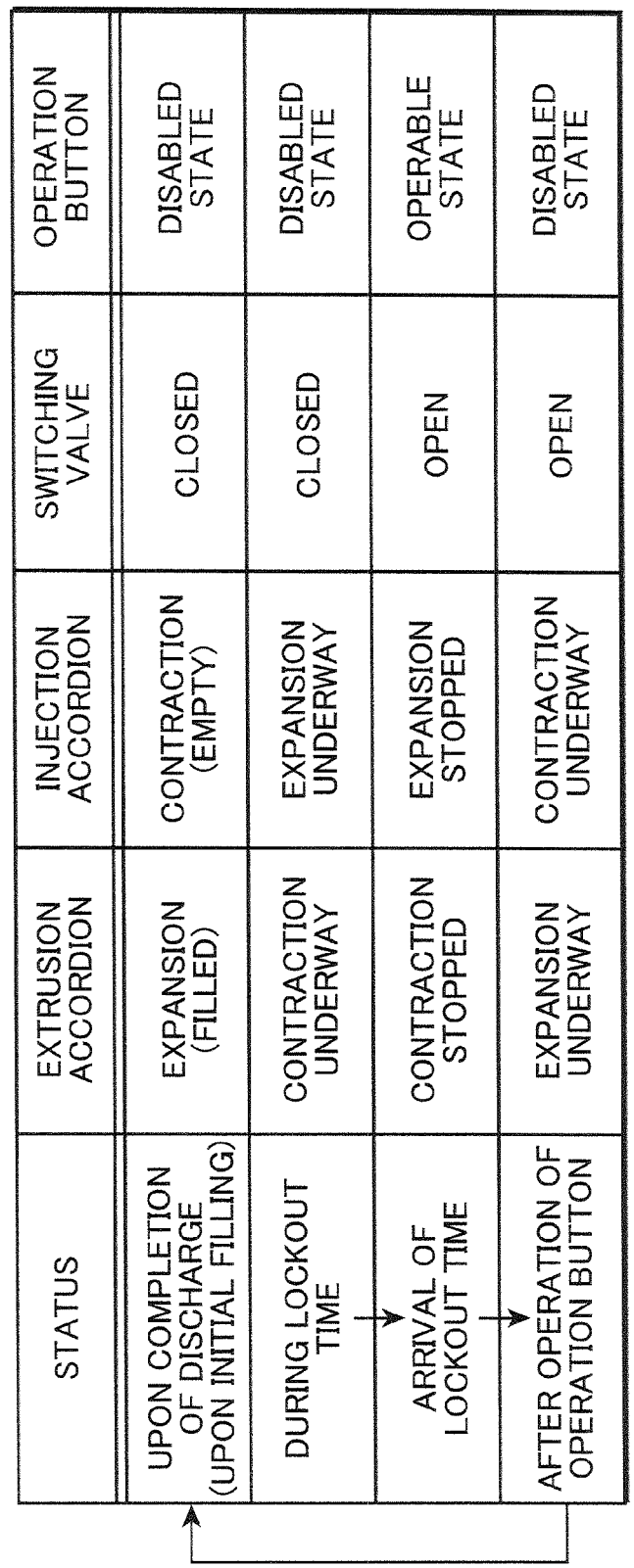
FIG. 7 is a list showing the states of FIG. 3 to FIG. 6.

The operation of the medical liquid injection system 1 is now explained with reference to FIG. 3 to FIG. 7. FIG. 3 is a cross section showing the operation of the injection equipment 3 depicted in FIG. 1, and shows the state after the discharge is complete (upon initial filling). FIG. 4 is a cross section showing the operation of the injection equipment 3 depicted in FIG. 1, and shows the state during the period of filling the medical liquid into the accordion container 6 for injection. FIG. 5 is a cross section showing the operation of the injection equipment 3 depicted in FIG. 1, and shows the state upon completion of filling the medical liquid into the accordion container 6 for injection. FIG. 6 is a cross section showing the operation of the injection equipment 3 depicted in FIG. 1, and shows the state when the operation button 12 is operated. FIG. 7 is a list showing the states of FIG. 3 to FIG. 6.

Referring to FIG. 3 and FIG. 7, when the medical liquid in the accordion container 6 for injection is completely delivered, or at the start of using the injection equipment 3, as shown with the arrow Y1, the medical liquid from the medical liquid pump 2 is introduced into the accordion container 5 for extrusion through the introductory hole 7f. The accordion container 5 for extrusion is thereby expanded. In accordance therewith, the connecting member 7 is pressed toward the accordion container 6 for injection as shown in arrow Y2, and causes the accordion container 6 for injection to contract. In the state of FIG. 3, the end (lower end of FIG. 3) of the operated part 14 of the switching valve 9 comes into contact with the bottom face of the accordion container 6 for injection (inner surface of the protruding part 6b) and is pushed upward, whereby the valve body 15 becomes a closed position. In addition, a predetermined amount (3 ml in this embodiment) of the medical liquid is introduced into the accordion container 6 for injection by taking a predetermined time (hereinafter referred to as the "lockout time") from the state of FIG. 3.

Referring to FIG. 4 and FIG. 7, the medical liquid introduced into the accordion container 5 for extrusion is introduced into the accordion container 6 for injection through the pore 8a of the adjustable member 8 as shown with the arrow Y3. Specifically, in this embodiment, since the diameter size E2 (refer to FIG. 3) of the accordion container 6 for injection is larger than the diameter size E1 (refer to FIG. 3) of the accordion container 5 for extrusion, the pressure receiving area in the housing chamber S2 for injection relative to the connecting member 7 is greater than the pressure receiving area in the housing chamber S1 for extrusion relative to the connecting member 7. In addition, the pressure of the medical liquid in both housing chambers S1, S2 is mutually equal in a state when the valve body 15 is in a closed position. Thus, the connecting member 7 is subject to force in the direction as shown in with the arrow Y4 which contracts the accordion container 5 for extrusion and expands the accordion container 6 for injection. By utilizing this force, the medical liquid is filled in the accordion container 6 for injection from the accordion container 5 for extrusion through the pore 8a. Note that the valve body 15 is inserted into the connecting part 7c of the connecting member 7 in an elastically deformed state. Thus, as a result of receiving the reactive force of the foregoing elastic deformation, the switching valve 9 follows the movement of the connecting member 7 shown with the arrow Y4.

In addition, when a predetermined amount of the medical liquid is filled in the accordion container 6 for injection (when the lockout time arrives), as shown in FIG. 5, the operated part 14 comes into contact with the bottom face (inner surface of the protruding part 5b) and the expansion of the accordion container 6 for injection is thereby restricted. In this state, the end (upper end of FIG. 5) of the operated part 14 is disposed more on the side of the operation button 12 than the positioning part 10a of the cylindrical container 10. Thus, the operated part 14 can be pushed in accordance with the pushing operation of the operation button 12. Contrarily, in the state of FIG. 3 and FIG. 4, the operated part 14 is disposed more on the inside than the positioning part 10a. Thus, even when the operation button 12 is pushed, the movement is restricted by the positioning part 10a, and the operated part 14 cannot be pushed (disabled state). As a result of causing the operation button 12 to be in a disabled state during the lockout time as described above, it is possible to prevent the medical liquid from being filled in an amount that is less than the predetermined amount.

After the lockout time has arrived as described above, the operation button 12 is pushed in the direction of the arrow Y5 as shown in FIG. 6. According to this operation, the operated part 14 becomes displaced relative to the connecting member 7 as shown with the arrow Y6, and the valve body 15 is thereby operated to the open position. Consequently, the medical liquid in the accordion container 6 for injection can be delivered from the delivery opening 7g as shown with the arrow Y7, and the pressure of the medial liquid in the accordion container 6 for injection becomes smaller than the pressure of the medical liquid in the accordion container 5 for extrusion. Accordingly, the accordion container 5 for extrusion expands due to the discharge pressure of the medical liquid pump 2, and the connecting member 7 is consequently pushed as shown with the arrow Y8. The accordion container 6 for injection is thereby contracted and a predetermined amount of the medical liquid in the accordion container 6 for injection is delivered.

As explained above, according to the medical liquid injection system 1, the housing chamber S2 for injection is contracted based on the expansion of the housing chamber S1 for extrusion according to the discharge pressure of the medical liquid based on the medical liquid pump 2, and it is therefore possible to deliver the medical liquid filled in the housing chamber S2 for injection. In other words, according to the medical liquid injection system 1, when the user operates the operation button 12 and switches the switching valve 9 to the open position, the medical liquid in the housing chamber S2 for injection can be delivered by using the discharge pressure of the medical liquid pump 2 without having to provide additional force. Thus, the force required for the user to deliver the medical liquid can be limited to the force required for switching the switching valve 9 to the open position. Thus, according to the present invention, it is possible to alleviate the force required for a user to inject a medical liquid.

In this embodiment, the pressure receiving areas of the housing chamber S1 for extrusion and the housing chamber S2 for injection are set so as to generate force in a direction of contracting the housing chamber S1 for extrusion and expanding the housing chamber S2 for injection in a state where the medical liquid is filled in the housing chamber S1 for extrusion and the housing chamber S2 for injection. Accordingly, the medical liquid from the medical liquid pump 2 can be reliably filled in the housing chamber S2 for injection. Specifically, when the medical liquid is discharged from the medical liquid pump 2, foremost, the medical liquid is preferentially filled in the housing chamber S1 for extrusion without going through the adjustable member 8 which causes pressure loss, and reactive force caused by the difference between the pressure receiving areas of both housing chambers S1, S2 is generated according to the foregoing filling of the medical liquid. Upon reaching a state where no more medical liquid can be filled in the housing chamber S1 for extrusion, the medical liquid will have no place to go. But since reactive force in a direction of expanding the housing chamber S2 for injection is generated in this situation, the medical liquid with no place to go is gradually introduced into the housing chamber S2 for injection through the adjustable member 8 by using the foregoing reactive force. In addition, when the switching valve 9 is switched to the open position, the delivery of the medical liquid via the delivery tube 17 is allowed and the inside of the housing chamber S2 for injection is decompressed. Thus, the pressure inside the housing chamber S1 for extrusion (discharge pressure caused by the medical liquid pump 2) becomes relatively higher than the pressure in the housing chamber S2 for injection, and the housing chamber S1 for extrusion thereby expands. The medical liquid in the housing chamber S2 for injection is thereby delivered.

Note that, while this embodiment generates the reactive force based on the difference of the pressure receiving areas of both housing chambers S1, S2, the present invention is not limited thereto. For example, the resilience of both accordion containers 5, 6 arising from the expansion or contraction from a state of their natural length in which external force is not being applied may also be used as the reactive force. This resilience can be adjusted by suitably setting the material or numbers of folds of both accordion containers 5, 6 or the thickness of the side wall of both accordion containers 5, 6.

This embodiment includes the adjustable member 8 as a member which configures the passage for causing the housing chamber S1 for extrusion and the housing chamber S2 for injection to be in communication. Consequently, while the housing chamber Si for extrusion is connected to the medical liquid pump 2 without going through the adjustable member 8, the housing chamber S2 for injection is connected to the medical liquid pump 2 via the housing chamber S1 for extrusion and the adjustable member 8.

Note that this embodiment includes the adjustable member 8 as a part of the injection equipment 3. Nevertheless, as in the embodiment described later, a flow controller (refer to reference numeral 26 of FIG. 8) connected to the injection equipment 3 may be provided separate from the injection equipment 3. According to the foregoing configuration, the lockout time of the injection equipment 3 can be suitably selected by changing the prescribed flow rate of the flow controller connected to the injection equipment 3.

In this embodiment, the switching valve 9 can be displaced by the operation button 12 in a state where a predetermined amount of the medical liquid is filled in the housing chamber S2 for injection, and the switching valve 9 cannot be displaced by the operation button 12 in a state where a predetermined amount of the medical liquid is not filled in the housing chamber S2 for injection. It is thereby possible to prevent the delivery of the medical liquid in an amount that is less than the predetermined amount. Thus, according to this embodiment, it is possible to reliably administer an amount (the predetermined amount) of medical liquid, which is prescribed in order to attain the intended effect, to the patient. Thus, it is possible to realize the effective administration of medical liquid, and prevent drawbacks of having to spend extra time to satisfy a predetermined amount of the medical liquid again as a result of initially delivering the medical liquid in an amount that is less than the predetermined amount.

In this embodiment, the switching valve 9 is switched from the open position to the closed position according to the contraction of the housing chamber S2 for injection that leads to the completion of delivery of the medical liquid via the delivery tube 17. In other words, the switching valve 9 can be automatically switched to the closed position upon the completion of the delivery of the medical liquid via the delivery tube 17. Thus, as a result of the user simply performing an operation of switching the switching valve 9 from the closed position to the open position, a predetermined amount of the medical liquid can be reliably administered to the patient. In addition, after the foregoing administration, the filling of the medical liquid into the housing chamber S2 for injection is automatically started.

Another embodiment according to the present invention is now explained with reference to FIG. 8 and FIG. 9.

Figure 8:
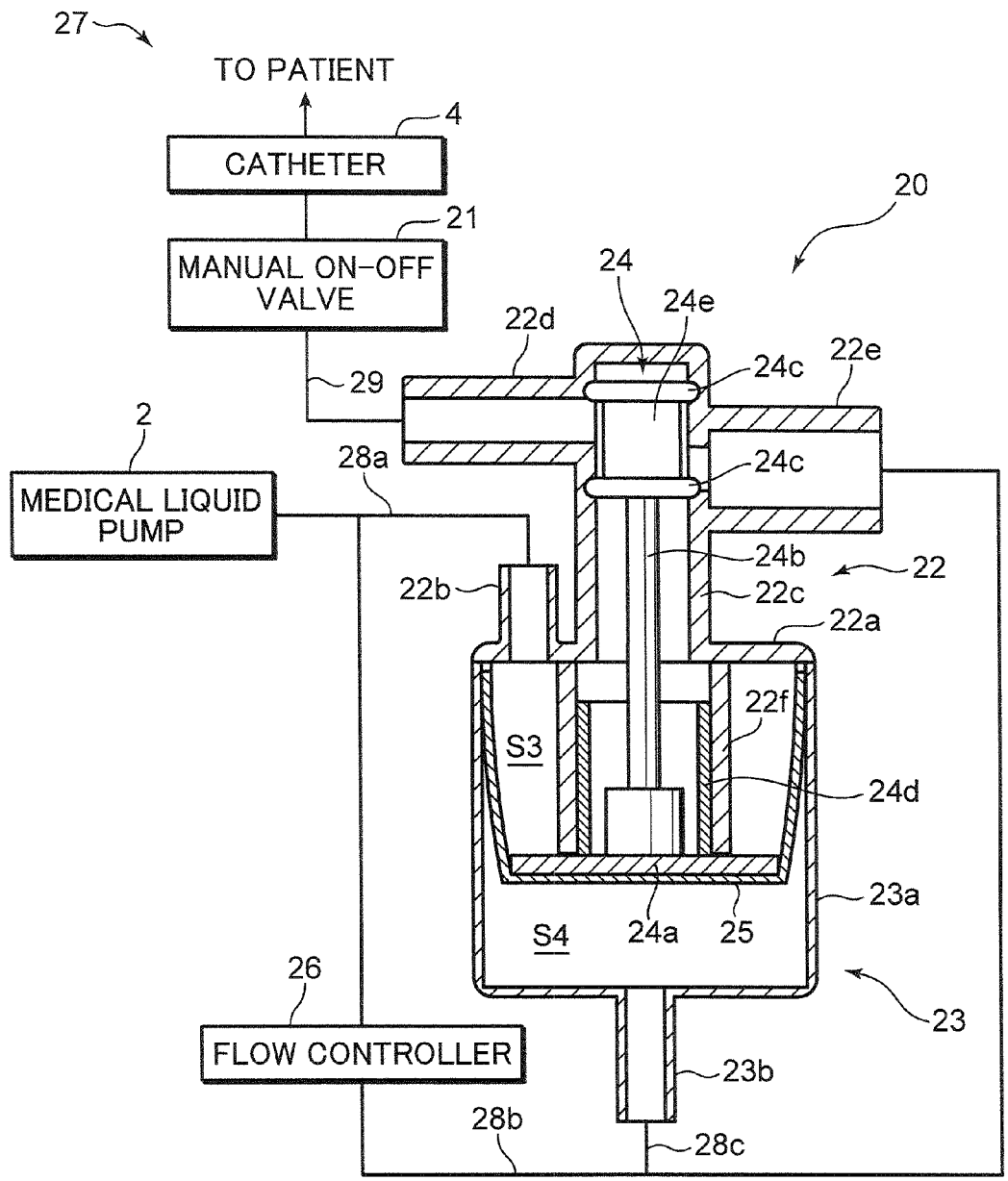
FIG. 8 is a schematic diagram showing the overall configuration of the medical liquid injection system according to another embodiment of the present invention.

FIG. 8 is a schematic diagram showing the overall configuration of the medical liquid injection system according to another embodiment of the present invention. FIG. 9 is a cross section showing the injection equipment of the medical liquid injection system depicted in FIG. 8. Note that the same configuration as in the foregoing embodiment is given the same reference numeral and the explanation thereof is omitted.

The medical liquid injection system 27 comprises the medical liquid pump 2, tubes 28a to 28c connected to the medical liquid pump 2, a flow controller (adjustable unit) 26 for controlling the flow rate of the medical liquid flowing through the tube 28b, an injection equipment 20 connected to the tube 28a and configured to fill the medical liquid from the medical liquid pump 2 and deliver a predetermined amount of medical liquid according to a user's operation, and a catheter 4 for guiding the medical liquid delivered from the injection equipment 20 to a patient.

The tube 28a causes the medical liquid pump 2 and the injection equipment 20 to be in direct communication. The tube 28b branches midway from the tube 28a and causes the medical liquid pump 2 and the injection equipment 20 to be in communication via the flow controller 26. The tube 28c branches from the tube 28b at the downstream side of the flow controller 26 and causes the medical liquid pump 2 and the injection equipment 20 to be in communication.

As with the adjustable member 8 of the foregoing embodiment, the flow controller 26 controls the flow rate of the medical liquid by generating a pressure loss in the medical liquid from the medical liquid pump 2.

The injection equipment 20 comprises a container body (container) 23 connected to the tube 28c, a lid body (container) 22 mounted on the container body 23 and connected to the tubes 28a and 28b, a displacement member 24 provided in a displaceable manner within the container body 23 and the lid body 22, a bulkhead 25 for partitioning the chamber (liquid housing chamber) in the container body 23 into a housing chamber S3 for extrusion and a housing chamber S4 for injection, a tube 29 for guiding the medical liquid delivered from the housing chamber S4 for injection, and a manual on-off valve (switching valve) 21 provided to the tube 29 and which allows or prevents the delivery of the medical liquid via the tube 29 according to the user's operation. Note that, for the sake of convenience of explanation, while the tube 28b and the tube 28c have been explained as components that are not a part of the configuration of the injection equipment 20, at least a portion of the tube 28b and the tube 28c which connects the connection 23b and the third connection 22e described later configures a part of the injection equipment 20 (part of the delivery passage).

The container body 23 comprises a cylindrical part 23a in which one end is open and the other end is closed, a connection 23b which protrudes from the bottom part of the cylindrical part 23a and which can connect to the tube 28c, and a hole which penetrates the bottom part of the cylindrical part 23a and the protruding part 23b. The medical liquid is introduced into the cylindrical part 23a via the hole from the tube 28c connected to the protruding part 23b.

The lid body 22 comprises a lid part 22a that is fixed to the cylindrical part 23a so as to cover the opening of the cylindrical part 23a, a first connection 22b for connecting the tube 28a to the lid part 22a, a protruding part 22c which protrudes from the lid part 22a toward a direction of becoming separated from the cylindrical part 23a, a second connection 22d and a third connection 22e which respectively extend laterally from the protruding part 22c, and a guide part 22f which extends from the lid part 22a into the cylindrical part 23a. The first connection 22b protrudes from the lid part 22a toward a direction of becoming separated from the cylindrical part 23a, and can be connected to the tube 28a. A through-hole is formed in the first connection 22b and the lid part 22a therethrough, and the medical liquid is introduced into the container body 23 from the tube 28a via such hole. The protruding part 22c is formed in a cylindrical shape in which its base end side opens to the inside of the container body 23 and in which its tip is closed. The second connection 22d is formed in a cylindrical shape which is in communication with the inside of the protruding part 22c, and can be connected to the tube 29. The third connection 22e is formed in a cylindrical shape which is in communication with the inside of the protruding part 22c at a position that is more close to the container body 23 than the second connection 22d, and can be connected to the tube 28b. The guide part 22f is disposed concentrically with the protruding part 22c, and is formed in a cylindrical shape which extends to roughly half the depth of the cylindrical part 23a of the container body 23.

The displacement member 24 comprises a support plate 24a disposed in the cylindrical part 23a of the container body 23, a rod 24b standing on the support plate 24a and in which its tip is disposed in the protruding part 22c of the lid body 22, an elastic body 24e provided to the tip of the rod 24b, and a guide tube 24d standing on the support plate 24a. The support plate 24a is formed in a disk shape having a diameter size that is larger than the guide part 22f of the lid body 22. The elastic body 24e includes a pair of flange parts 24c which contacts tightly to the inner surface of the protruding part 22c of the lid body 22 and restricts the circulation of the medical liquid. The circulation of the medical liquid is allowed between the respective flange parts 24c. The guide tube 24d has a diameter size so that it can slide within the guide part 22f of the lid body 22, and is disposed in the guide part 22f.

Figure 9:
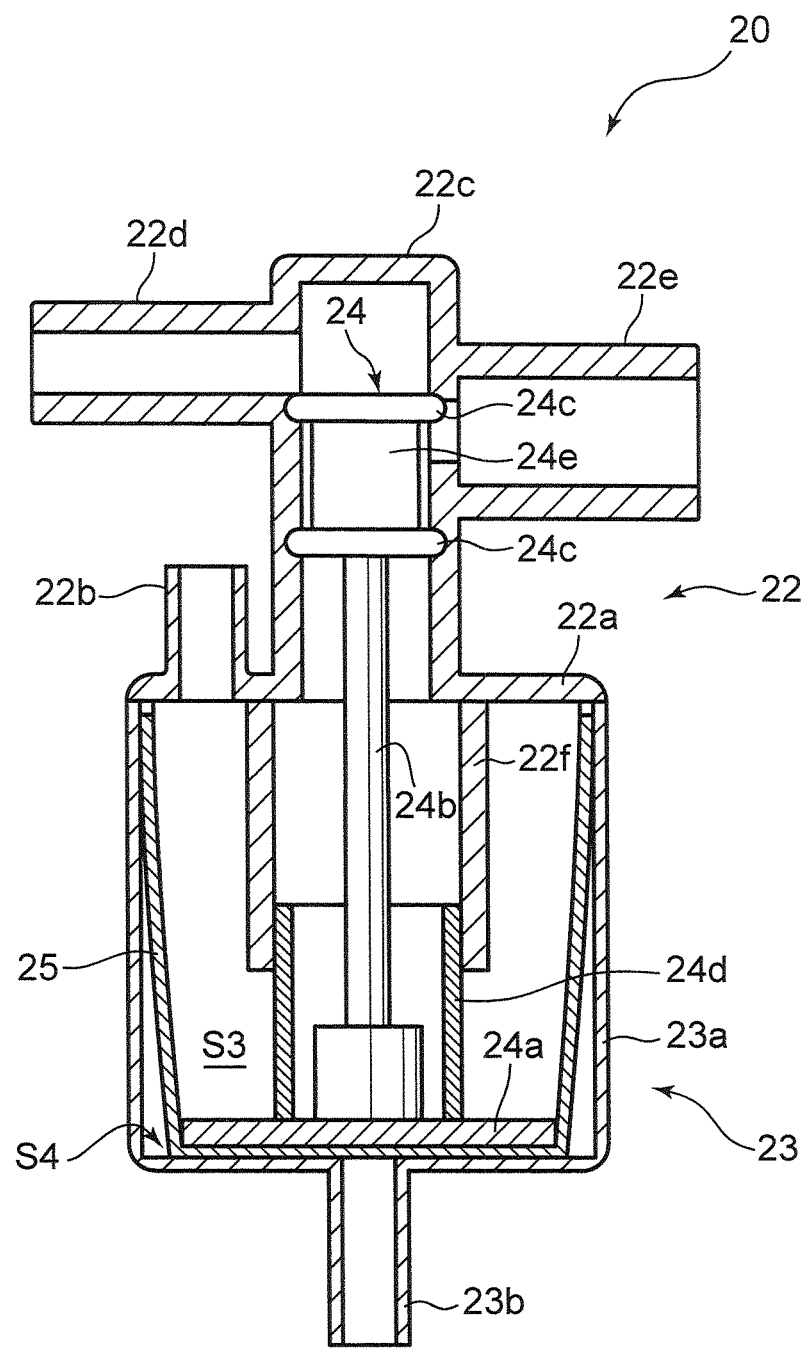
FIG. 9 is a cross section showing the injection equipment of the medical liquid injection system depicted in FIG. 8.

In addition, the displacement member 24 can be displaced relative to the container body 23 and the lid body 22 between an open position where the support plate 24a comes into contact with the end face of the guide part 22f of the lid body 22 as shown in FIG. 8, and a closed position where the support plate 24a comes into contact with the bottom part of the cylindrical part 23a via the bulkhead 25 as shown in FIG. 9. Here, in the open position, the pair of flange parts 24c of the elastic body 24e is disposed so as to sandwich the opening of the second connection 22d and the third connection 22e as shown in FIG. 8, and the circulation of the medical liquid between both connections 22d, 22e is allowed. Moreover, in the closed position, the flange part 24c on the tip side of the elastic body 24e is disposed between the second connection 22d and the third connection 22e as shown in FIG. 9, and the circulation of the medical liquid between both connections 22d, 22e is restricted. Note that, in both the open position and the closed position, since the flange part 24c on the base end side of the elastic body 24e is disposed more on the base end side than the second connection 22d and the third connection 22e, the circulation of the medical liquid between the protruding part 22c and the container body 23 is restricted.

The bulkhead 25 is a circular thin film made of elastic synthetic resin (silicone resin, for instance). The peripheral part of the bulkhead 25 is fixed in a state of being sandwiched between the lid part 22a of the lid body 22 and the open end of the cylindrical part 23a of the container body 23. Moreover, the central part of the bulkhead 25 is supported by the support plate 24a of the displacement member 24. Accordingly, the bulkhead 25 generates elastic force (reactive force) to return to the open position shown in FIG. 8 in a state where the medical liquid is introduced into the housing chamber S3 for extrusion as shown in FIG. 9.

The manual on-off valve 21 is a switching valve having a valve element that is normally closed and opened according to the user's pressing operation. Specifically, in a state before the manual on-off valve 21 is operated, the flow of the medical liquid between the tube 29 and the catheter 4 is restricted. Meanwhile, as a result of the manual on-off valve 21 being operated, the flow of the medical liquid between the tube 29 and the catheter 4 is allowed.

The operation of the medical liquid injection system 27 is now explained.

As shown in FIG. 8, in a state where the displacement member 24 is in the open position, the medical liquid from the medical liquid pump 2 is introduced into the housing chamber S3 for extrusion via the tube 28a preferentially to the tube 28b in which pressure loss is generated by the flow controller 26. Pursuant to the introduction of the medical liquid into the housing chamber S3 for extrusion, the bulkhead 25 is subject to elastic deformation (extended), and at the same time the displacement member 24 is displaced to a closed position as shown in FIG. 9. From this state, the medical liquid from the medical liquid pump 2 is introduced into the tube 28b via the flow controller 26.

Specifically, since the manual on-off valve 21 is normally closed, the medical liquid from the flow controller 26 is introduced into the housing chamber S4 for injection via the tube 28c. In addition, when the lockout time that is defined by the flow rate adjusted by the flow controller 26 elapses, the open position shown in FIG. 8 is achieved and a predetermined amount of the medical liquid is introduced into the housing chamber S4 for injection. Here, the reason why the medical liquid is introduced into the housing chamber S4 for injection is because the elastic force of return to the open position works on the bulkhead 25.

In addition, by operating the manual on-off valve 21, the delivery of the medical liquid via the tube 29 is allowed, and the pressure inside the housing chamber S4 for injection is reduced. Thus, the pressure in the housing chamber S3 for extrusion, which is the discharge pressure of the medical liquid pump 2, becomes relatively higher than the pressure in the housing chamber S4 for injection. Consequently, the housing chamber S3 for extrusion expands and the housing chamber S4 for injection contracts. According to this operation, the predetermined amount of medical liquid in the housing chamber S4 for injection is delivered via the catheter 4.

This embodiment comprises a container configured from the container body 23 and the lid body 22, and a bulkhead 25 having higher retractility than the container, and which partitions the chamber inside the container into the housing chamber S3 for extrusion and the housing chamber S4 for injection. When the medical liquid is supplied from the medical liquid pump 2, one of both housing chambers S3, S4 expands while the other contracts as a result of the bulkhead 25 expanding and contracting. Accordingly, as a result of the bulkhead 25 expanding so that the housing chamber S3 for extrusion contracts based on the discharge pressure of the medical liquid pump 2, the medical liquid in the housing chamber S4 for injection can be delivered.

Note that the specific embodiments described above mainly include the invention configured as described below.

In order to achieve the foregoing object, the present invention provides an injection equipment which is to be connected to a discharge unit capable of discharging a pressured medical liquid, and which fills the medical liquid from the discharge unit and delivers a predetermined amount of the medical liquid according to a user's operation, the injection equipment comprising: an introductory passage which is connectable to the discharge unit and which is used for guiding the medical liquid from the discharge unit; a housing chamber for extrusion which is capable of housing the medical liquid guided by the introductory passage and which is expandable according to the housing of the medical liquid; a housing chamber for injection which can be communicated with the discharge unit via an adjustable unit for adjusting a flow rate of the medical liquid discharged from the discharge unit and which expands according to the housing of the medical liquid, and which can deliver the housed medical liquid by being contracted; a delivery passage for guiding the medical liquid delivered from the housing chamber for injection to a patient; a switching valve capable of performing a switching operation between a closed position for preventing the delivery of the medical liquid through the delivery passage, and an open position for allowing the delivery of the medical liquid through the delivery passage; and an operating part capable of switching the switching valve from the closed position to the open position by receiving operation of a user in a state where the predetermined amount of medical liquid is housed in the housing chamber for injection, wherein the housing chamber for extrusion and the housing chamber for injection are mutually connected so that, when one of the chambers expands, the other one of the chambers contracts, and wherein, by switching the switching valve to the open position in a state where at least the predetermined amount of medical liquid is filled in the housing chamber for injection, the housing chamber for injection is contracted based on the expansion of the housing chamber for extrusion according to the discharge pressure from the discharge unit so as to deliver the predetermined amount of medical liquid.

According to the present invention, the housing chamber for injection is contracted based on the expansion of the housing chamber for extrusion according to the discharge pressure from the discharge unit so as to deliver the predetermined amount of medical liquid filled in the housing chamber for injection. In other words, according to the present invention, when the user operates the operating part and switches the switching valve to the open position, the medical liquid in the housing chamber for injection can be delivered by using the discharge pressure of the discharge unit without having to provide additional force. Thus, the force required for the user to deliver the medical liquid is limited to the force required for switching the switching valve to the open position. Thus, according to the present invention, it is possible to alleviate the force required for a user to inject a medical liquid.

In the injection equipment, preferably, the housing chamber for injection and the housing chamber for extrusion generate reactive force in a direction of expanding the housing chamber for injection and also contracting the housing chamber for extrusion in accordance with the introduction of the medical liquid into the housing chamber for extrusion.

According to the foregoing configuration, the medical liquid from the discharge unit can be reliably filled in the housing chamber for injection. Specifically, in the foregoing configuration, when the medical liquid is discharged from the discharge unit, foremost, the medical liquid is preferentially filled in the housing chamber for extrusion without going through the adjustable unit which causes pressure loss, and reactive force in a direction of expanding the housing chamber for injection is generated according to the foregoing filling of the medical liquid. Upon reaching a state where no more medical liquid can be filled in the housing chamber for extrusion, the medical liquid will have no place to go, but since reactive force in a direction of expanding the housing chamber for injection is generated, the medical liquid with no place to go is gradually introduced into the housing chamber for injection through the adjustable unit by using the foregoing reactive force. In addition, when the switching valve is switched to the open position, the delivery of the medical liquid via the delivery passage is allowed and the inside of the housing chamber for injection is decompressed. Thus, the pressure inside the housing chamber for extrusion (discharge pressure caused by the discharge unit) becomes relatively higher than the pressure in the housing chamber for injection, and the housing chamber for extrusion thereby expands. The medical liquid in the housing chamber for injection is thereby delivered.

In order to generate the reactive force, for example, pressure receiving areas are set to the housing chamber for injection and the housing chamber for extrusion respectively so as to generate force in a direction of expanding the housing chamber for injection and also contracting the housing chamber for extrusion in a state where pressure is applied to the housing chamber for injection and the housing chamber for extrusion by the discharge unit.

Preferably, the injection equipment further comprises the adjustable unit for configuring at least a part of a passage for causing the housing chamber for extrusion and the housing chamber for injection to be communicated with each other.

Accordingly, as a result of the housing chamber for extrusion and the housing chamber for injection being connected via the adjustable unit, the housing chamber for extrusion is connected to the discharge unit without going through the adjustable unit, and the housing chamber for injection is connected to the discharge unit via the housing chamber for extrusion and the adjustable unit.

In the injection equipment, preferably, the switching valve comprises a valve body, and an operated part which extends from the valve body and can displace the valve body from a closed position to an open position by engaging with the operating part, and the operating part and the operated part are engageable in a state where the predetermined amount of medical liquid is housed in the housing chamber for injection, and, when the medical liquid housed in the housing chamber for injection is less than the predetermined amount by a pre-set amount, the engagement of the operating part and the operated part is restricted by the housing chamber for extrusion that has expanded corresponding to the amount of such shortage in liquid amount.

According to the foregoing configuration, even if the operating part is operated while the predetermined amount of medical liquid is being filled in the housing chamber for injection, the closed position of the valve body is maintained. Accordingly, it is possible to prevent the delivery of the medical liquid that is less than a predetermined amount. Accordingly, it is possible to reliably administer an amount (predetermined amount) of medical liquid, which is prescribed in order to attain the intended effect, to the patient. Thus, it is possible to realize the effective administration of medical liquid, and prevent drawbacks of having to spend extra time to satisfy a predetermined amount of the medical liquid as a result of initially delivering the medical liquid in an amount that is less than the predetermined amount.

In the injection equipment, preferably, the switching valve is switched from the open position to the closed position according to the contraction of the housing chamber for injection that leads to the completion of delivery of the medical liquid via the delivery passage.

According to the foregoing configuration, the switching valve can be automatically switched to the closed position upon the completion of the delivery of the medical liquid via the delivery passage. Thus, as a result of the user simply performing an operation of switching the switching valve from the closed position to the open position, a predetermined amount of the medical liquid can be reliably administered to the patient. In addition, after the foregoing administration, the filling of the medical liquid into the housing chamber for injection is automatically started.

Preferably, the injection equipment further comprises an accordion container for injection and an accordion container for extrusion capable of respectively expanding and contracting along a predetermined telescopic shaft, and a fixing member for fixing positions of outer end faces of the accordion container for injection and the accordion container for extrusion which are mutually separated in a state where the accordion container for injection and the accordion container for extrusion are arranged in series so that these containers can expand and contract along a common telescopic shaft, and the housing chamber for injection is provided inside the accordion container for injection, and the housing chamber for extrusion is provided inside the accordion container for extrusion.

In other words, the accordion container for injection and the accordion container for extrusion are arranged in a series so that they can expand and contract along a common telescopic shaft, and the positions of the outer end faces of both accordion containers are fixed. Consequently, the movement of the inner end faces of both accordion containers facing each other can be mutually coordinated.

Preferably, the injection equipment further comprises a container including a liquid housing chamber capable of housing the medical liquid, and a bulkhead which has higher retractility than the container, and which partitions the liquid housing chamber into the housing chamber for injection and the housing chamber for extrusion.

In other words, the housing chamber for extrusion and the housing chamber for injection are partitioned by a bulkhead having higher retractility than the container. Consequently, as a result of the bulkhead expanding and contracting, one of both housing chambers will expand while the other will contract. Accordingly, as a result of the bulkhead expanding so as to contract the housing chamber for extrusion based on the discharge pressure of the discharge unit, the medical liquid in the housing chamber for injection can be delivered.

Moreover, the present invention provides a medical liquid injection system comprising a discharge unit capable of discharging a pressured medical liquid, and the injection equipment connected to the discharge unit.

INDUSTRIAL APPLICABILITY

According to the present invention, it is possible to alleviate the force required for a user to inject a medical liquid.

The invention claimed is:

1. An injection equipment which is to be connected to a discharge unit capable of discharging a pressured medical liquid, and which fills the medical liquid from the discharge unit and delivers a predetermined amount of the medical liquid according to operation of a user,
the injection equipment comprising:
an introductory passage which is connectable to the discharge unit and which is used for guiding the medical liquid from the discharge unit;
a housing chamber for extrusion which is capable of housing the medical liquid guided by the introductory passage and which is expandable according to the housing of the medical liquid;
a housing chamber for injection which can communicate with the discharge unit via an adjustable unit for adjusting a flow rate of the medical liquid discharged from the discharge unit and which expands according to the housing of the medical liquid, and which can deliver the housed medical liquid by being contracted;
a delivery passage for guiding the medical liquid delivered from the housing chamber for injection to a patient;
a switching valve capable of performing a switching operation between a closed position for preventing the delivery of the medical liquid through the delivery passage, and an open position for allowing the delivery of the medical liquid through the delivery passage; and
an operating part capable of switching the switching valve from the closed position to the open position by receiving operation of the use in a state where the predetermined amount of medical liquid is housed in the housing chamber for injection,
wherein the housing chamber for extrusion and the housing chamber for injection are mutually connected so that, when one of the chambers expands, the other one of the chambers contracts,
wherein, by switching the switching valve to the open position in a state where at least the predetermined amount of medical liquid is filled in the housing chamber for injection, the housing chamber for injection is contracted based on the expansion of the housing chamber for extrusion according to the discharge pressure from the discharge unit so as to deliver the predetermined amount of medical liquid, and
wherein the housing chamber for injection and the housing chamber for extrusion generate reactive force in a direction of expanding the housing chamber for injection and also contracting the housing chamber for extrusion in accordance with the introduction of the medical liquid into the housing chamber for extrusion.

2. The injection equipment according to claim 1, wherein pressure receiving areas are set to the housing chamber for injection and the housing chamber for extrusion respectively so as to generate force in a direction of expanding the housing chamber for injection and also contracting the housing chamber for extrusion in a state where pressure is applied to the housing chamber for injection and the housing chamber for extrusion by the discharge unit.

3. The injection equipment according to claim 1, further comprising the adjustable unit for configuring at least a part of a passage for causing the housing chamber for extrusion and the housing chamber for injection to be communicated with each other.

4. The injection equipment according to claim 1,
wherein the switching valve comprises a valve body, and an operated part which extends from the valve body and can displace the valve body from a closed position to an open position by engaging with the operating part, and
wherein the operating part and the operated part are engageable in a state where the predetermined amount of medical liquid is housed in the housing chamber for injection, and, when the medical liquid housed in the housing chamber for injection is less than the predetermined amount by a pre-set amount, the engagement of the operating part and the operated part is restricted by the housing chamber for extrusion that expanded corresponding to the amount of such shortage in liquid amount.

5. The injection equipment according to claim 1, wherein the switching valve is switched from the open position to the closed position according to the contraction of the housing chamber for injection that leads to the completion of delivery of the medical liquid via the delivery passage.

6. The injection equipment according to claim 1, further comprising:
an accordion container for injection and an accordion container for extrusion capable of respectively expanding and contracting along a predetermined telescopic shaft; and
a fixing member for fixing positions of outer end faces of the accordion container for injection and the accordion container for extrusion which are mutually separated in a state where the accordion container for injection and the accordion container for extrusion are arranged in series so that these containers can expand and contract along a common telescopic shaft,
wherein the housing chamber for injection is provided inside the accordion container for injection, and the housing chamber for extrusion is provided inside the accordion container for extrusion.

7. The injection equipment according to claim 1, further comprising:
a container including a liquid housing chamber capable of housing the liquid; and
a bulkhead which has higher retractility than the container, and which partitions the liquid housing chamber into the housing chamber for injection and the housing chamber for extrusion.

8. A medical liquid injection system, comprising:
a discharge unit capable of discharging a pressured medical liquid; and
the injection equipment according to claim 1 connected to the discharge unit.

* * * * *